United States Patent
Machado De Castro et al.

(10) Patent No.: US 11,560,579 B2
(45) Date of Patent: Jan. 24, 2023

(54) METHOD FOR PRETREATING LIGNOCELLULOSIC BIOMASS

(71) Applicants: PETRÓLEO BRASILEIRO S.A.—PETROBRAS, Rio de Janeiro (BR); UNIVERSIDADE FEDERAL DO RIO DE JANEIRO—UFRJ, Rio de Janeiro (BR)

(72) Inventors: Aline Machado De Castro, Rio de Janeiro (BR); Sonia Maria Cabral De Menezes, Rio de Janeiro (BR); Luiz Silvino Chinelatto Junior, Rio de Janeiro (BR); Alessandra Rangel Cassella, Rio de Janeiro (BR); Bernardo Dias Ribeiro, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 0 days.

(21) Appl. No.: 17/251,623

(22) PCT Filed: Jun. 7, 2019

(86) PCT No.: PCT/BR2019/050213
§ 371 (c)(1),
(2) Date: Dec. 11, 2020

(87) PCT Pub. No.: WO2019/237169
PCT Pub. Date: Dec. 19, 2019

(65) Prior Publication Data
US 2021/0388405 A1  Dec. 16, 2021

(30) Foreign Application Priority Data

Jun. 11, 2018 (BR) .......................... 1020180117416

(51) Int. Cl.
*C12P 19/04* (2006.01)
*C12P 19/14* (2006.01)

(52) U.S. Cl.
CPC .............. *C12P 19/14* (2013.01); *C12P 19/04* (2013.01); *C12P 2201/00* (2013.01)

(58) Field of Classification Search
CPC ..................................................... C12P 19/04
See application file for complete search history.

(56) References Cited

U.S. PATENT DOCUMENTS

2008/0190013 A1   8/2008  Argyropoulos et al.

OTHER PUBLICATIONS

An et al., "Pretreatment of lignocellulosic biomass with renewable cholinium ionic liquids: Biomass fractionation, enzymatic digestion and ionic liquid reuse", Bioresource Technology, 192: 165-171, 2015.
Asakawa et al., "Cholinium ionic liquid/cosolvent pretreatment for enhancing enzymatic saccharification of sugarcane bagasse", Industrial Crops and Products, 86: 113-119, 2016.
de Castro et al., "Design and Characterization of Novel Choline-Based Phthalic Salts: A Case Study for Sugarcane Bagasse Pretreatment", Chemistry Select, 2: 8039-8042, 2017.
Hou et al., "Effect of anion structures on cholinium ionic liquids pretreatment of rice straw and the subsequent enzymatic hydrolysis", Biotechnology and Bioengineering, 112: 65-73, 2015.
International Search Report and Written Opinion in International Application No. PCT/BR2019/050213, dated Aug. 20, 2019, 12 pages (partial English Translation).
Liu et al., "Preparation of sugarcane bagasse cellulosic phthalate using an ionic liquid as reaction medium", Carbohydrate Polymers, 68(1): 17-25, 2007.
Brandt et al. (Dec. 19, 2012) "Deconstruction of Lignocellulosic Biomass with Ionic Liquids", Green Chemistry, 15(3):550-583.
Perez-Pimienta et al. (Jan. 2013) "Comparison of the Impact of Ionic Liquid Pretreatment on Recalcitrance of Agave Bagasse and Switchgrass", Bioresource Technology, 127:18-24.
Sluiter et al. (Aug. 2012) "Determination of Structural Carbohydrates and Lignin in Biomass", National Renewable Energy Laboratory (NREL), 18 pages.

*Primary Examiner* — Maryam Monshipouri
(74) *Attorney, Agent, or Firm* — Mintz Levin Cohn Ferris Glovsky and Popeo, P.C.

(57) ABSTRACT

The present invention describes a process for pretreatment of lignocellulosic biomass that comprises the step of contacting a lignocellulosic biomass with an ionic liquid consisting of a phthalic salt of dicholine in the weight ratio from 1:1 to 1:100 of biomass:ionic liquid, said step taking place for a period of time that varies from 0.4 to 48 hours and in a temperature range that varies from 60 to 200° C. Furthermore, the present invention also relates to the use of the pretreated lignocellulosic biomass in an enzymatic hydrolysis process.

12 Claims, 6 Drawing Sheets

METHOD FOR PRETREATING LIGNOCELLULOSIC BIOMASS

CROSS-REFERENCE TO RELATED APPLICATIONS

This application is a national stage application, filed under 35 U.S.C. § 371, of PCT International Patent Application No. PCT/BR2019/050213, filed on Jun. 7, 2019, and claims benefit of priority to Brazilian Application No. 10 2018 011741 6, filed on Jun. 11, 2018, the disclosures of all of which are incorporated herein by reference in their entirety.

FIELD OF THE INVENTION

The present invention relates to a process for pretreatment of lignocellulosic biomass using ionic liquids consisting of phthalic salts and to the use of the pretreated biomass in an enzymatic hydrolysis process.

BACKGROUND OF THE INVENTION

In the search for sustainable alternatives to replace petroleum derivatives, the use of lignocellulosic biomass as a raw material or energy source is an attractive resource owing to its great availability and its low cost.

The lignocellulosic materials may be waste products, such as sugar cane bagasse and maize straw; hardwood, such as aspen and poplar; coniferous wood, such as pine and fir; cellulosic wastes, such as recycled paper pulp and newsprint; herbaceous biomass, such as alfalfa hay and reed canary grass; municipal solid waste; among others.

By fermentation of the sugars derived from this type of biomass, for example, it is possible to release a wide range of bioproducts, such as ethanol, succinic acid, lactic acid, 2,3-butanediol, citric acid, acetic acid, itaconic acid, fumaric acid, n-butanol, among others.

However, the chemical composition of the lignocellulosic materials makes it difficult to produce these derivatives directly by fermentation, since they are polymers of complex carbohydrates basically consisting of cellulose $(C_6H_{10}O_5)_x$, hemicellulose $(C_5H_8O_4)_m$ and lignin $(C_9H_{10}O_3(OCH_3))_n$.

To facilitate access to the carbohydrates in the biomass for biological conversion, thus maximizing fermentation of the sugars, it is necessary to apply some pretreatment on the biomass for solubilization and separation of one or more of its components, especially lignin.

The pretreatment of the biomass has the following objectives: to reduce the degree of polymerization of the cellulose molecules, to make them accessible for the hydrolysis process, to avoid the formation of byproducts that are inhibitors of the processes of hydrolysis and fermentation, and primarily, to be economically viable.

At present there are various methods of pretreatment, which may be physical, chemical or physicochemical.

The chemical pretreatments may employ organic or inorganic compounds, normally employing acids, bases or organic solvents.

Ionic liquids also represent a promising alternative as solvents in the chemical pretreatment of biomass.

Brandt et al., in "Deconstruction of lignocellulosic biomass with ionic liquids"—Green Chem., 2013, 15, 550-583, describe a biomass pretreatment that uses ionic liquids as solvents. The ionic liquids described comprise cations selected from imidazoles, pyridine, piperidine, pyrrolidine, ammonium, sulfonic and phosphonium, and anions selected from sulfates, sulfonates, bromides, chlorides, iodides, acetates, phosphates and cyanamides.

The investigation by Perez-Pimienta et al., in "Comparison of the impact of ionic liquid pretreatment on recalcitrance of agave bagasse and switchgrass"—Bioresource Technology 127 (2013) 18-24, also describes ionic liquids as being excellent solvents for the pretreatment of lignocellulosic biomass. The ionic liquid assessed in this work was 1-ethyl-3-methyl imidazole acetate in various concentrations.

However, solvents based on imidazoles present risks with respect to the operational safety of the reaction, besides having the disadvantage of the occurrence of parallel reactions of degradation, both in laboratory processes and in industrial processes.

Therefore an aim of the present invention is to provide an alternative chemical pretreatment of lignocellulosic biomass that does not have the drawbacks identified in the prior art.

SUMMARY OF THE INVENTION

The present invention relates to a process for chemical pretreatment of lignocellulosic biomass using, as a solvent, an ionic liquid consisting of a phthalic salt of dicholine.

Said process comprises contacting an ionic liquid consisting of a phthalic salt of dicholine with the lignocellulosic biomass in the weight ratio from 1:1 to 1:100 of biomass:ionic liquid for a period of time that varies from 0.4 to 48 hours and in a temperature range that varies from 60° C. to 200° C.

Furthermore, the present invention is also directed at the use of the lignocellulosic biomass pretreated with the phthalic salt in an enzymatic hydrolysis process.

BRIEF DESCRIPTION OF THE FIGURES

The detailed description presented hereunder refers to the appended figures, where.

DETAILED DESCRIPTION OF THE INVENTION

The present invention relates to a process for chemical pretreatment of lignocellulosic biomass that employs an ionic liquid consisting of a phthalic salt of dicholine.

Said process comprises the step of contacting a lignocellulosic biomass with an ionic liquid consisting of a phthalic salt of dicholine in the weight ratio from 1:1 to 1:100 of biomass:ionic liquid.

Said contacting step takes place for a period of time that varies from 0.4 to 48 hours and at a temperature varying from 60° C. to 200° C.

In a preferred embodiment, the ionic liquid is selected from the salts dicholine phthalate, dicholine isophthalate and dicholine terephthalate. Preferably, the ionic liquid employed is selected from dicholine isophthalate and dicholine terephthalate.

The phthalic salts of dicholine described in the present invention are defined as being ionic liquids, as it was verified that these salts are in liquid form at the operating temperatures.

The salt dicholine isophthalate $[Ch]_2[Iso]$, for example, proved to be fluid at temperatures below 100° C. The kinematic and dynamic viscosities of this salt at various temperatures less than or equal to 100° C. are presented in Table 1 below.

TABLE 1

Viscosity of the salt $[Ch]_2[Iso]$ at different temperatures

| Temperature (° C.) | Kinematic (mm² · s⁻¹) | Dynamic (mPa · s) |
|---|---|---|
| 70 | 4909 | 5762 |
| 80 | 2190 | 2555 |
| 90 | 1185 | 1377 |
| 100 | 699 | 808 |

The salt dicholine terephthalate $[Ch]_2[Ter]$, in its turn, did not melt or prove to be fluid at temperatures less than or equal to 100° C.

Therefore definition of the operating temperature will depend on the salt used, it being certain that it will have to be high enough to guarantee classification of the salt as an ionic liquid.

In the process disclosed here, stirring may be employed in a range from 100 to 400 rpm. Preferably, the stirring employed is of about 250 rpm.

In a preferred embodiment, the process comprises a subsequent step of phase separation selected from centrifugation, filtration and decanting. In this step there is formation of a solid fraction and a liquid fraction.

The liquid fraction comprises liquors from the pretreatment, such as extracted lignin, free sugars, acetic acid, as well as furfural and 5-hydroxymethylfurfural (5-HMF).

The solid fraction contains the pretreated biomass with lower lignin content together with the excess phthalic salt used.

The process of the invention described here may also comprise the steps of washing and drying of said solid fraction, with the aim of removing the excess phthalic salt used and extracting possible components physically attached to the solid fraction, such as the residual lignin.

In the washing step, water, ethanol or a mixture thereof is used, and from 1 to 10 washing cycles may be carried out.

The drying step takes place at a temperature that varies from 60 to 200° C., preferably around a temperature of 80° C.

The lignocellulosic biomass to be employed in the pretreatment process disclosed here may be selected from waste products, hardwood, coniferous wood, cellulosic wastes, herbaceous biomass, and municipal solid waste. Preferably, sugar cane bagasse is used.

The present invention also relates to the use of the lignocellulosic biomass pretreated with an ionic liquid consisting of a phthalic salt in a treatment process of enzymatic hydrolysis.

In a preferred embodiment, cellulase enzymes are employed in the hydrolysis process, thus obtaining sugars such as glucose, xylose and cellobiose.

These sugars are very important in industrial fermentation processes for forming bioproducts, such as ethanol, 2,3-butanediol, n-butanol, lactic acid, succinic acid, citric acid, acetic acid, itaconic acid and fumaric acid.

The description given hereunder will be based on preferred embodiments of the invention. As will be obvious to a person skilled in the art, the invention is not limited to these particular embodiments.

EXAMPLES

Example 1—Pretreatment Process

The effects of the process for pretreatment of sugar cane bagasse using the ionic liquids dicholine isophthalate $[Ch]_2[Iso]$ and dicholine terephthalate $[Ch]_2[Ter]$ in the weight ratios from 1:5 to 1:100 of biomass:ionic liquid were assessed.

A reactor was employed consisting of 6 glass vessels arranged on a silicon carbide block, model Mettler-Toledo XT Plus™, which was connected to an IKA© RET Basic plate for heating and magnetic stirring and to a controller system, model IKA© ETS-D4 fuzzy controller.

The process was carried out at a temperature of 90° C. for a period of 24 hours. The magnetic stirring employed was 250 rpm.

After the step of contacting the ionic liquid with the biomass, the sample was centrifuged, obtaining a liquid fraction (pretreatment liquors) and a solid fraction.

The solid fraction was washed exhaustively with distilled water until the phthalic salts had been removed, and was then dried at 80° C. until low moisture content was verified.

Example 1a—Characterization of the Liquors from the Pretreatment

The liquors obtained after the pretreatment were analyzed by high-performance liquid chromatography (HPLC), Ultimate 3000 model from Thermo Scientific, with the aim of identifying the possible presence of free sugars, as well as furfural, 5-hydroxymethylfurfural (5-HMF) and acetic acid. The chromatographic conditions used were as follows:

BioRad HPX-87H column;
mobile phase: $H_2SO_4$ 5 mM, flow rate: 0.7 mL/min;
sample injection volume: 20 μL;
column temperature: 65° C.;
detector: RID at 35° C.; and
analysis time: 25 min.

Furthermore, the liquid fraction also underwent scanning spectrophotometric analysis, in a Thermo Scientific spectrophotometer, model Multiskan GO, in the wavelength range 200-500 nm, for investigation for the presence of lignin.

Figure 1:
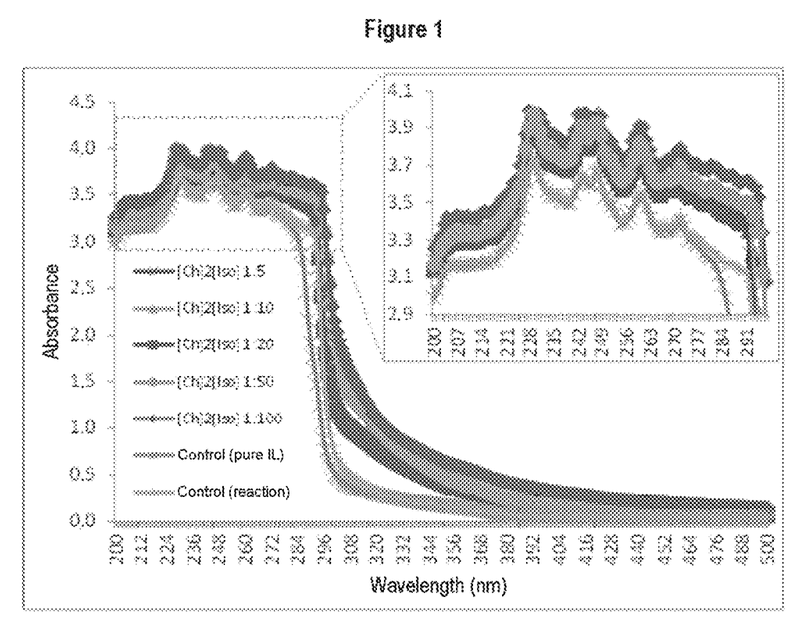
FIG. 1 shows the result of scanning spectrophotometric analysis carried out on the liquid fraction obtained after pretreatment of the biomass with dicholine isophthalate ionic liquid, comparing against control samples.

In the scanning spectrophotometric analysis in a wide wavelength range, shown in FIG. 1, it was possible to observe that the liquors from the pretreatment had a maximum value of absorbance of about 228-230 nm.

The above range is very close to the wavelength proposed by Sluiter et al., in the document "Determination of structural carbohydrates in lignin in biomass", 2012, for the analysis of lignin (acid-soluble) in samples of sugar cane bagasse (NIST standard sample).

Comparing them with the control samples, it can be seen that the curves presented in FIG. 1 have higher values of absorbance in the liquors of the samples that were submitted to incubation with the sugar cane bagasse.

Therefore the extraction of lignin (acid-soluble) during the pretreatment is verified.

Figure 2:
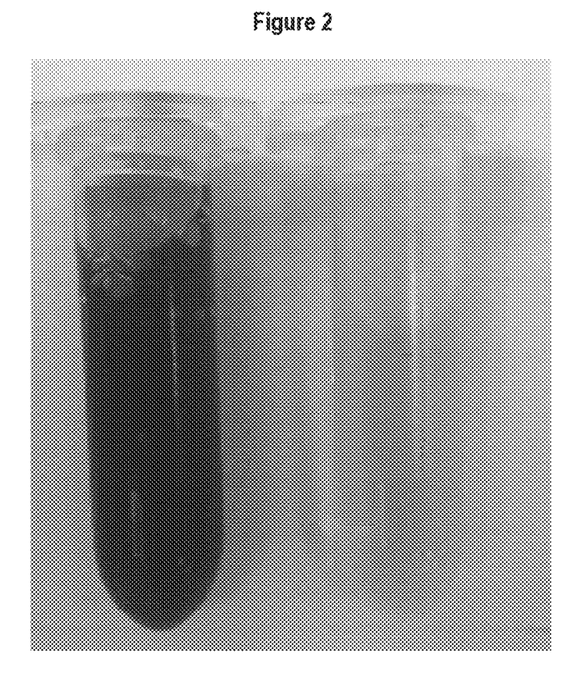
FIG. 2 shows a photograph of the liquors from pretreatment of sugar cane bagasse in the ratio of 1:100 with dicholine isophthalate (sample on the left) and in the ratio of 1:20 with dicholine terephthalate (sample on the right).

Moreover, visual observation of the liquors shown in FIG. 2 confirmed the results of scanning spectrophotometry. It is possible to verify solutions that are visibly darker after the pretreatment with [Ch]$_2$[Iso], thus indicating differentiated removal of lignin.

Example 1b—Characterization of the Pretreated Samples

The solid fractions of the samples of bagasse after the steps of contacting with the ionic liquid, centrifugation, washing and drying, were metalized with Au/Pd in a metalizer, model Quorum Q150TES, and then were analyzed by scanning electron microscopy (SEM) in a Zeiss EVO-LS15 microscope, at a voltage of 20 kV.

Figure 3:
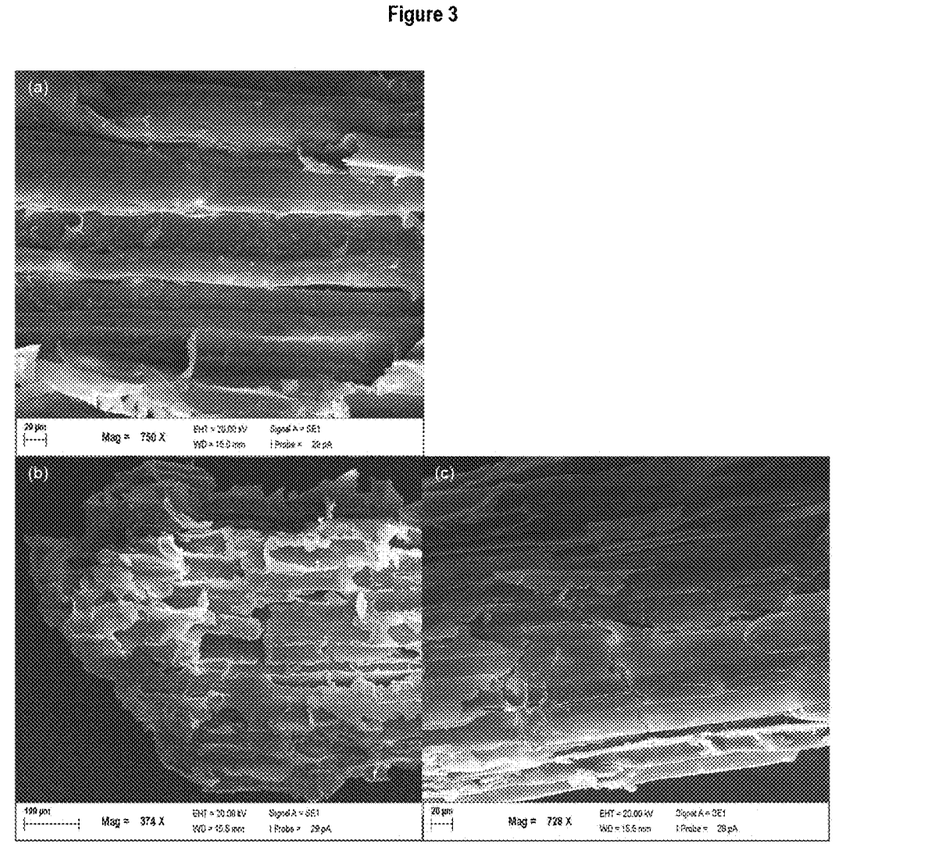
FIG. 3 shows images obtained in scanning electron microscopy (SEM) of samples of natural sugar cane bagasse (a) and bagasse pretreated with dicholine terephthalate in the ratios of 1:10 (b) and 1:20 (c).
Figure 4:
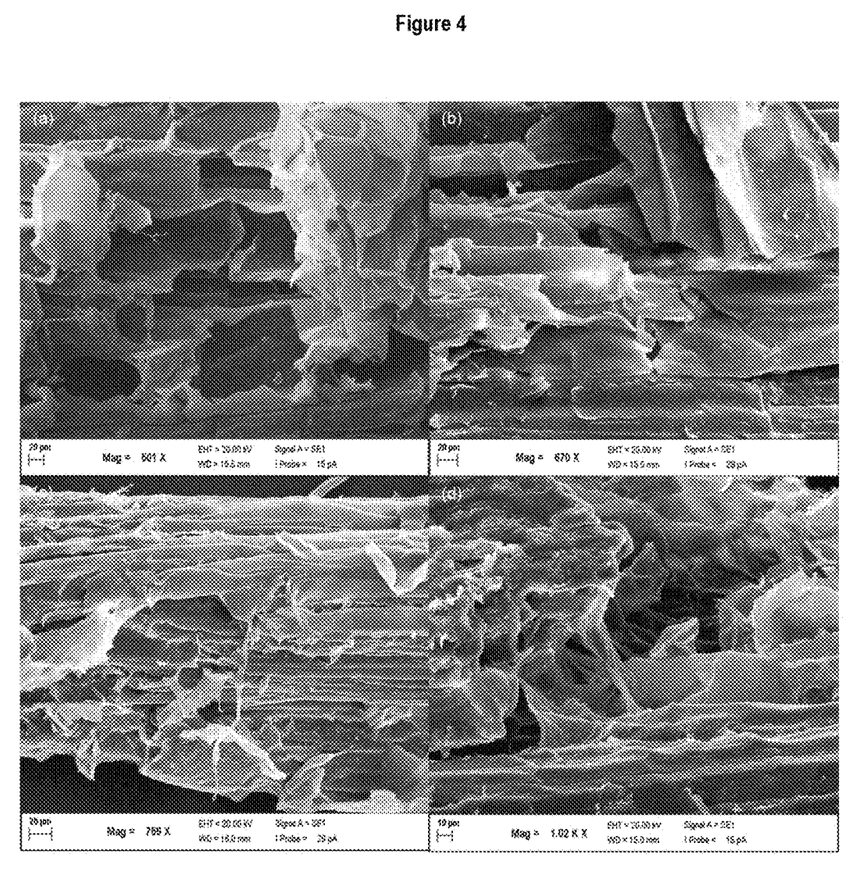
FIG. 4 shows images obtained in scanning electron microscopy (SEM) of samples of sugar cane bagasse pretreated with dicholine isophthalate in the ratios of 1:5 (, b) and 1:10 (c, d).
Figure 5:
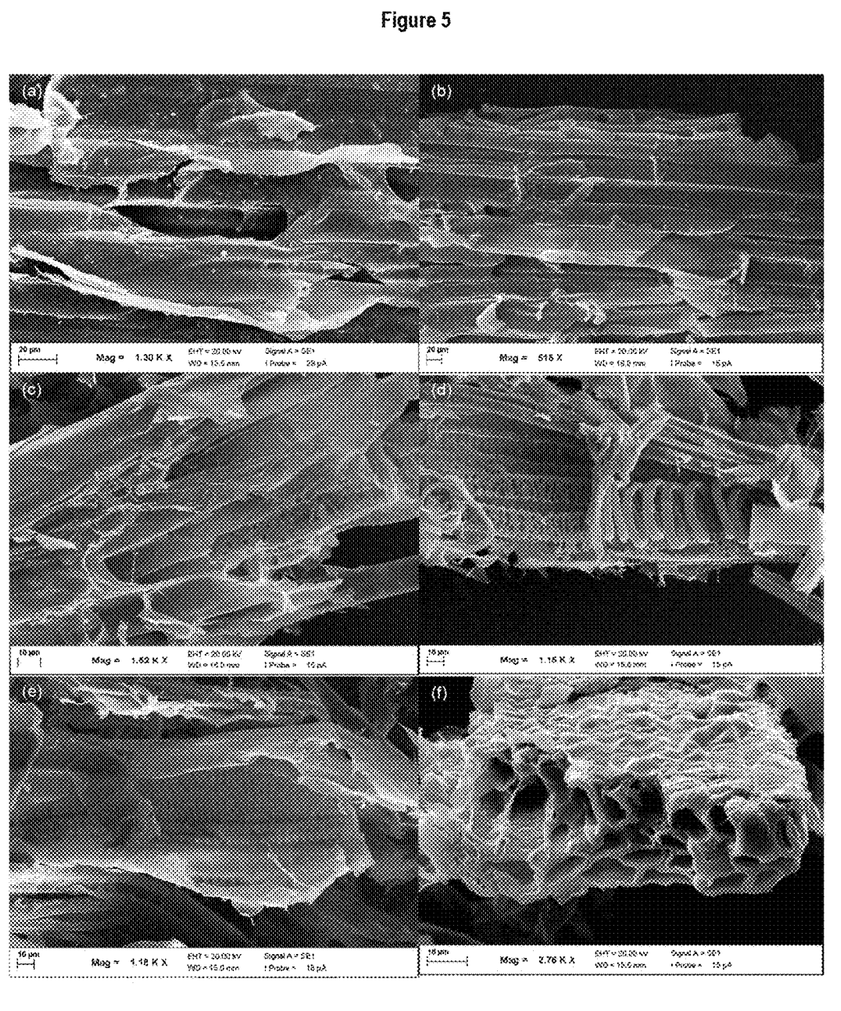
FIG. 5 shows images obtained in scanning electron microscopy (SEM) of samples of sugar cane bagasse pretreated with dicholine isophthalate in the ratios of 1:20 (, b), 1:50 (c, d) and 1:100 (e, f).

The results of the SEM analysis are presented in FIGS. 3, 4 and 5.

The figures show very disorganized bagasse fibers, with formation of cavities and tunnels, consistent in their extent with the higher proportion of [Ch]$_2$[Iso] employed in the pretreatment (4 and 5).

The samples incubated with the salt [Ch]$_2$[Ter] were also observed, and showed fibers that were a little less affected, with morphology a little more rigid and compact.

The solid samples were also submitted to thermogravimetric analysis TGA/DTA, with the aim of determining the composition (carbohydrates and lignin). The equipment used was SDTQ 600. The heating rate was 20° C.·min$^{-1}$ and the flow rate of N$_2$ was 100 mL·min$^{-1}$, in the temperature range from 25 to 500° C., followed by an isotherm of 30 min. Next, it was heated again with an airstream of 100 mL·min$^{-1}$ to 1000° C.

Table 2 below illustrates the percentage change in the contents of lignin and cellulose in the samples pretreated with the phthalic salt.

TABLE 2

Percentage change in the contents of lignin and cellulose in the samples pretreated with the phthalic salt.

| Type and proportion of the ionic liquid used | Change, %, relative to the bagasse | |
|---|---|---|
| | Cellulose | Lignin |
| [Ch]$_2$[Ter] 1:10 | +6% | −23% |
| [Ch]$_2$[Ter] 1:20 | +8% | −49% |
| [Ch]$_2$[Iso] 1:5 | +1% | −8% |
| [Ch]$_2$[Iso] 1:10 | −1% | −2% |
| [Ch]$_2$[Iso] 1:20 | +4% | −28% |
| [Ch]$_2$[Iso] 1:50 | +9% | −81% |
| [Ch]$_2$[Iso] 1:100 | +5% | −24% |

It can be seen that the contents of cellulose increased in practically all the samples, while the contents of lignin decreased in all of them, compared to the contents of these components in the non-pretreated sugar cane bagasse.

Figure 6:
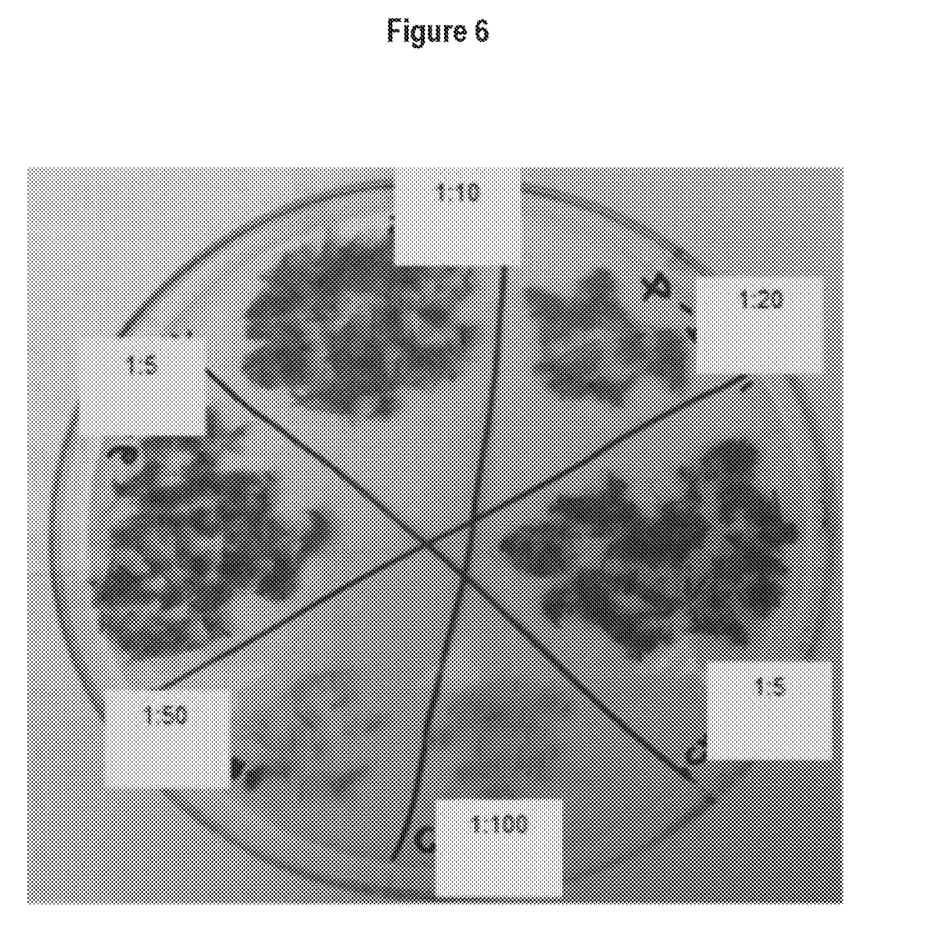
FIG. 6 shows a photograph of the solid samples obtained after pretreatment with the dicholine isophthalate ionic liquid.

In FIG. 6 it is possible to verify the visual appearance of the pretreated biomasses, with notable differences in the tonality of the materials. It can be seen that, in general, the higher the proportion of [Ch]$_2$[Iso] employed in the pretreatment, the clearer the sample.

It was therefore concluded that removal of lignin is greater for higher proportion of the salt [Ch]$_2$[Iso], since lignin is the main component responsible for the amber coloration of the biomass.

Example 2—Use of the Pretreated Biomass in an Enzymatic Hydrolysis Process

The solid fractions of the samples of bagasse after the steps of contacting with the ionic liquid, centrifugation, washing and drying were submitted to the enzymatic hydrolysis process so as to measure the benefit of the pretreatment proposed here.

The reaction was carried out in equipment of the hybridizer type (model Combi-D24, FINEPCR), at 50° C. and with stirring at 25 rpm.

The reaction medium consisted of 100 mM sodium citrate buffer at pH 5.0 and the commercial enzyme Cellic CTec3© (supplied by Novozymes), added in a loading of 4.2% (volume of preparation/sample weight).

The initial content of bagasse pretreated in the reaction was just 1% (w/v) and samples were taken during the period from 24 to 96 hours of reaction.

Figure 7:
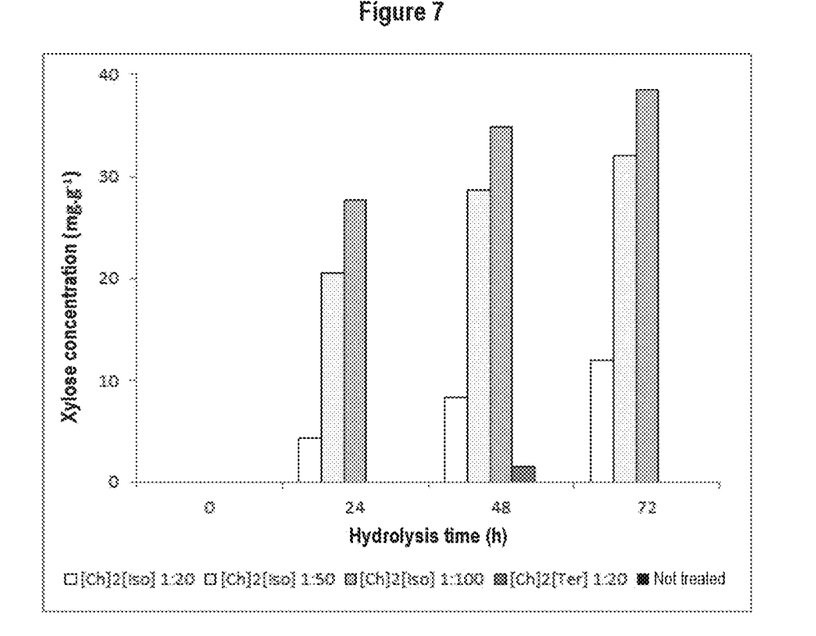
FIG. 7 shows the concentrations of xylose during enzymatic hydrolysis of the pretreated samples and of a sample without pretreatment of sugar cane bagasse.
Figure 8:
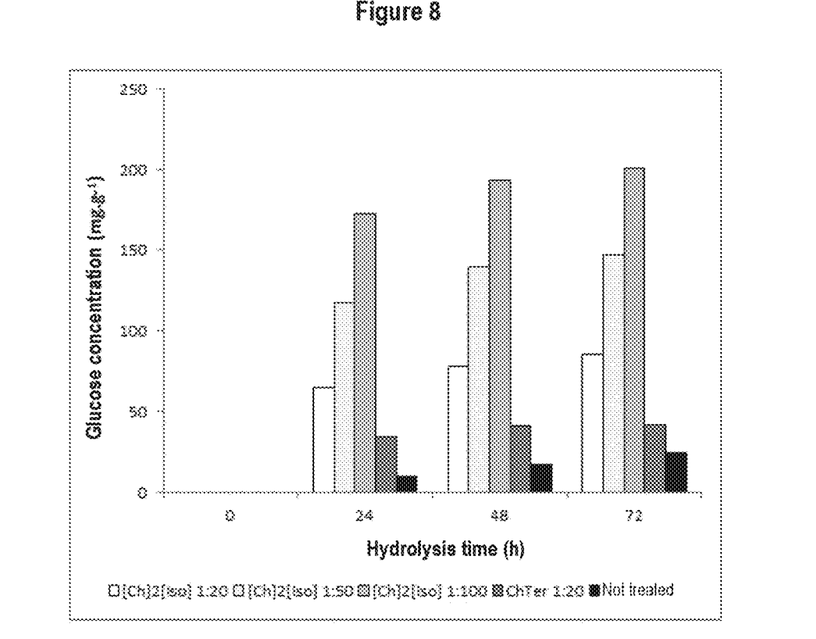
FIG. 8 shows the concentrations of glucose during enzymatic hydrolysis of the pretreated samples and of a sample without pretreatment of sugar cane bagasse.

As can be seen in FIGS. 7 and 8, the concentration of glucose released by the hydrolysis was increased by up to 8.1 times, relative to the glucose released by the sample of bagasse that had not undergone the pretreatment with the ionic liquid. The concentrations are expressed on the basis of the weight fraction of sugar per dried pretreated biomass.

The description that has been given up to here, of the subject matter of the present invention is to be regarded as just one possible embodiment or possible embodiments, and any particular features introduced therein are only to be understood as something that was written to facilitate understanding. Accordingly, they are not to be considered in any way as limiting the invention, which is limited to the scope of the claims that follow.

The invention claimed is:

1. A process for treatment of lignocellulosic biomass, the process comprising:
    contacting the lignocellulosic biomass with an ionic liquid consisting of a phthalic salt of dicholine in the weight ratio from 1:1 to 1:100 of biomass:ionic liquid to produce a mixture.

2. The process as claimed in claim 1, wherein contacting the lignocellulosic biomass with an ionic liquid takes place for a period of time that varies from 0.4 to 48 hours and in a temperature range that varies from 60 to 200° C.

3. The process as claimed in claim 1, characterized in that the ionic liquid is selected from the salts dicholine phthalate, dicholine isophthalate and dicholine terephthalate.

4. The process as claimed in claim 1, further comprising stirring the mixture in a range from 100 to 400 rpm.

5. The process as claimed in claim 4, wherein the stirring is at 250 rpm.

6. The process as claimed in claim 1, further comprising a subsequent step of phase separation selected from centrifugation, filtration and decanting the mixture to obtain a liquid fraction and a solid fraction.

7. The process as claimed in claim 6, further comprising washing and drying of said solid fraction, wherein the washing takes place with water, ethanol or a mixture thereof, from 1 to 10 cycles, and wherein the drying takes place at a temperature that varies from 60 to 200° C.

8. The process as claimed in claim 7, wherein the drying takes place at a temperature of 80° C.

9. The process as claimed in claim 1, wherein the lignocellulosic biomass is selected from waste products, hardwood, coniferous wood, cellulosic wastes, herbaceous biomass, and municipal solid waste.

10. The process as claimed in claim 9, wherein the lignocellulosic biomass is sugar cane bagasse.

11. A process comprising:
   enzymatic hydrolysis of the solid fraction obtained by the process of claim 6.

12. The process as claimed in claim 11, wherein the enzymatic hydrolysis uses cellulase enzymes in a reaction medium.

\* \* \* \* \*